United States Patent [19] [11] 4,233,291
Simon-Lavoine et al. [45] Nov. 11, 1980

[54] NOVEL BIOLOGICAL SUBSTANCE FROM A FUNGUS AND THE PROCESS FOR PRODUCING THE SAME

[75] Inventors: Nicole Simon-Lavoine, Neuilly; Marcel Forgeot, Paris, both of France

[73] Assignee: Science Union et Cie, Suresnes, France

[21] Appl. No.: 964,071

[22] Filed: Nov. 27, 1978

[30] Foreign Application Priority Data

Nov. 30, 1977 [FR] France ................................ 77 36000

[51] Int. Cl.$^3$ .................... A61K 37/00; C07C 103/52; C12P 21/00
[52] U.S. Cl. ............................ 424/177; 260/112.5 R; 435/68
[58] Field of Search .......................... 424/177; 435/68; 260/112.5 R

[56] References Cited

FOREIGN PATENT DOCUMENTS 847941 11/1975 Belgium .................................... 424/177

OTHER PUBLICATIONS

Chemistry, Biological, 3148–B.
Chem. Abst., 86, 1977, 2070x.
Biological Abstr., 63, 18908.

Primary Examiner—Delbert R. Phillips
Attorney, Agent, or Firm—Omri M. Behr

[57] ABSTRACT

This invention relates to a biological substance extracted from the Mycelium of a Fusarium. This substance has a peptidolic structure with specific amino-acids into.

This invention also relates to a process for producing the afore-said biological substance by culturing the strain of Fusarium and extracting the mycelium.

The biological substance has a therapeutical use.

17 Claims, No Drawings

NOVEL BIOLOGICAL SUBSTANCE FROM A FUNGUS AND THE PROCESS FOR PRODUCING THE SAME

PRIOR ART

The relevant prior art may be illustrated with the following references:
Belgian patent, 847 941
J of Antibioties, 29 (1976) 1043
J of Antibioties, 29 (1976) 1050
Tetrahedron, 14 (1978) 1147

SUMMARY OF THE INVENTION

This invention provides a biological substance obtained by extracting the mycelium produced during the cultures of a Fusarium equiseti.

This biological substance contains four different components denominated A, B, C and D of peptidolic structure. Only the specific amino-acids vary from one component to another one.

This substance is produced by culturing a strain of Fusarium equiseti under specific conditions, separating the mycelium and extracting it with water unsoluble organic solvents. The biological substance is further purified according to the usual methods of the biochemistry.

This substance is of value for the immunological therapy and is used in the form of pharmaceutical compositions, namely those suitable for parenteral, permucous, per cutaneous, sublingual or rectal ways.

PREFERRED EMBODIMENT OF THE INVENTION

This invention relates to a novel biological substance extracted from a fungus.

More precisely, this invention provides a biological substance obtained from the brothes of a Fusarium, a method for its production and its use in the form of pharmaceutical compositions.

This invention specifically provides a biological substance having a peptidolic structure obtained by extraction from the mycelium of Fusarium equiseti. This biological substance includes four different components having a very close structure and giving rise to the production by hydrolysis in acidic medium of a single hydroxy acid, α-hydroxy valeric acid and of specific α-amino acids i.e. N-methyl Valine, N-methyl isoleucine and N-methyl allo iso leucine.

The percentage of these four components named A, B, C, D has been determined after separation by high pressure liquid-chromatography in reverse phase, by means of an integrator. The percentage of four components in this biological substance is determined by measuring the square of each peak after high pressure liquid chromatography and the residual absorption in UV light at 254 μm.

The respective percentages of each component may slightly vary and in average range between the following figures:
component A, 2–5%
component B, 10–16%
component C, 32–39%
component D, 40–47%

Component A after partial hydrolysis in alkaline medium provides 3 mol of the lactone of α-hydroxy isovaleroyl N-methyl Valine. This lactone results from the splitting of the ester functions and recyclizing of the liberated hydroxy group into a lactone.

Component A after complete hydrolysis in acidic medium produces 3 moles of N-methyl Valine and 3 moles of α-hydroxy isovaleric acid. The acid hydrolysis produces both a split of the ester functions and of the amid functions.

Component B after partial hydrolysis in alkaline medium gives raise to the production of 2 moles of the lactone of α-hydroxy isovaleroyl N-methyl Valine and a mole of the lactone of α-hydroxy isovaleroyl N-methyl isoleucine (or N-methyl isoalloleucine).

Component C under similar experimental conditions provides after partial hydrolysis 2 moles of the lactone of α-hydroxy iso valeroyl N-methyl isoleucine (or N-methyl alloisoleucine) and 1 mole of the lactone of α-hydroxy iso valeroyl N-methyl valine.

The complete hydrolysis in acidic medium gives rise to the production of 3 moles of α-hydroxy isovaleric acid, 1 mole of N-methyl valine and 2 moles of N-methyl isoleucine (or N-methyl alloisoleucine).

Compound D provides after partial hydrolysis in alkaline medium 3 moles of the lactone of α-hydroxy isovaleroyl N-methyl isoleucine (or N-methyl alloisoleucine).

After complete hydrolysis in acidic medium, compound D provides 3 moles of α-hydroxy isovaleric acid and 3 moles of N-methyl iso leucine (or N-methyl alloisoleucine). In summary, the complete hydrolysis of the depsipeptide according to the invention, provides α-hydroxy isovaleric acid, N-methyl valine, N-methyl iso leucine (erythro form) and N-methyl allo isoleucine (threo form). The N-methyl allo isoleucine has not yet been attributed to one specific component of the biological substance.

This biological substance of peptidolic structure may be obtained by sumitting to an aerobic fermentation a culture of Fusarium equiseti in determined conditions of temperature, stirring and duration, separating at the end of the time of fermentation the mycelium of Fusarium equiseti from the broth, extracting the mycelium with a water-insoluble organic solvent, separating the organic phases, evaporating off, taking up the crude residue with a liquid hydrocarbon, submitting the organic solution to a counter-current extraction with a mixture of water and a lower alkanol, separating this alkanolic phase, concentrating it and recovering the biological substance which is further purified by the usual physical or chemical methods.

The process of preparation according to the invention may also be defined by the following features, which are the presently preferred ones:
the strain of Fusarium equiseti responsible of the production of the depsipeptide according to the invention is that of Fusarium equiseti (Corda) saccardo, deposited at the Commonwealth Mycological Institute at Kew (Surrey) Great Britain under the n 213 107.
the aerobic fermentation is carried out in three stages at a pH between 5 and 6 and for a period of time extending from 36 to 48 hours for each stage.
the extraction of the mycelium of Fusarium equiseti is performed using a chlorinated organic solvent as for example Trichlorethylene.
the taking up of the crude residue is performed using a saturated liquid hydrocarbon such as hexane or pentane.

the purification of the peptidolic substance is performed by means of chromatography on silica.
the hydrosoluble alkanol is methanol or ethanol.

The depsipeptide according to the invention is endowed with interesting pharmacological properties. It possesses strong immuno-modulating properties evidenced by a positive response in the test of hypersensitivity to 4-ethoxy methylene 2-phenyloxazolone or to lipopolysaccharides of Escherichiacoli. Further the depsipeptide causes the activation of macrophages by increasing or altering the enzymatic activities and the total proteic content of the cells thereof. Moreover, the depsipeptide show an anti-exsudative and anti-oedematious activity.

Compared to the activities of Muramyldipeptide and of the lipopolysaccharides from Escherichia coli, the depsipeptides from Fusarium equiseti appears to be at least as active as these two reference substances.

The depsipeptide according to this invention find a use in human or veterinary therapy, namely as a stimulant of the body defences. It is particularly useful for the treatment of the chronic or acute diseases of the respiratory tract such as chronic bronchitis and emphysema.

For the therapeutic use, the depsipeptide is incorporated into pharmaceutical compositions with an inert non-toxic pharmaceutically-acceptable carrier or vehicle. The carriers or vehicles are those suitable for administration parenteral, permucous, percutaneous or rectal way.

As preferred pharmaceutical compositions they may be cited the injectible solutions or suspensions, the sublingual tablets, the solutions or suspensions in a diffusible solvent to be applied on the mucosa optionally under pressure, the solutions in a polar solvent for the percutaneous way and the suppositories.

The useful dosology may broadly vary depending of the therapeutic use, the way of administration, the weight or age of the patient. In the man, the usual dosology ranges from 0.05 and 1 mg per unit dosage and the daily dosage ranges from 0.2 and 5 mg.

It may also be convenient to utilize discontinuous administrations such as from 2 to 4 successive administrations followed with a stay for several weeks and renewed again 2 to 4 times.

The pharmaceutical compositions according to the invention may also contain further active ingredients having similar activities, or synergistic activities; they also may contain diluing agents, filling agents, binding agents, flavouring agents, sweetening agents, tensioactive agents, emulsifiers or suspending agents and propelling agents.

The pharmaceutical compositions are prepared according to the known methods of pharmacotechnology.

The following examples are merely intended to illustrate the invention:

EXAMPLE 1

Production of the depsipeptide from Fusarium equiset.

(A) Identication of the strain

The strain of Fusarium equiseti which allows the production of the depspeptide has been identified as a Fusarium equiseti (Corda) Saccardo and deposited at the Commonwealth Mycological Institute at Kew under the No. 213,107.

(a) fermentation brothes and mycelial growth

For the purpose of identifying this strain it appears convenient to use the following methods of fermentation (1) fermentation medium n°1

This medium is constituted from

| saccharose | 25g |
| glucose | 25g |
| ammonium nitrate | 10g |
| magnesium nitrate | 2,5g |
| mono potassium phosphate | 5g |
| water enough for | 1000ml |

This medium is sterilized and the pH value is adjusted after sterilization to about 5.

After inoculation this medium gives raise to the production of a vary dense mycelium, of a wooly appearance, and showing at its surface an orange colouration. At the reverse face in a Petri box thallus shows a yellow-orange colouration, better known as a peach colouration turning to yellowish-orange in the aged cultures.

In the cultures on gelose it, appears a yellow pigment which diffuses therein.

(2) cultures on atomized corn steep (2%) agar-agar (2%) medium

In this medium the mycelium grows in producing a thallus appearing as rather close-shaved, wooly with concentric typical zonings. Pigmentation remains slight. The back free shows in the age a dark-yellowish colouration.

(3) cultures on carboxy methyl cellulose (Capellin + Petterson's Medium 1965) This medium is constituted with the following ingredients:

| carboxymethyl cellulose | 15g |
| ammonium nitrate | 1g |
| monopotassium phoshate | 1g |
| magnesium sulphate | 5g |
| yeast extract | 1g |

Distilled water enough for 1000 ml

This medium may be optionaly added to small pieces of dry leaves of Phragmites communes.

On this medium the mycelium remains scarce, very-close-shaved, nearly unpercievable and colourless.

(b) effect of the light on the sporulation of the strain

Out the three above described medium under illumination, with white light during 12 hours per day only the medium containing carboxy methyl cellulose and further the medium in which leaves of Phragmites communes are added, gives rise to the formation of macroconidias.

High amounts of macroconidias are formed in the culture media in Petri box enlighted with a Wood light diffuser (max. wawe lengths 360 and 365 μm) disposed at 33 cm from the lamp, after an incubation period of 4 to 6 days. The colouration of the media after culture under Wood light is slightly attenuated in comparison to that appearing in the cultures grown uner white light.

(c) aspects of the Fusarium in several medias

Fusarium equiseti N° 213,107 has also been grown on usual media, generally utilized for the growth of various Fusarium. Experimental results have been thus obtained:
- medium containing 40 g/l of flour of oat
- medium containing 50 g of grated potatoes, 10 g glucose and 20 g gelose for 1 liter water
- medium containing 2% Agar and Malt On these media, it appears that the conidiogenesis occurs with a very slight extend with production of abnormous conidias which could induce the confusion between aborted macroconidias with microconidias.

It may be of interest to note some typical aspects of the Fusarium genus, namely the appearance of a pigment distributed in concentric zonings. This coloured zones appear namely in the medium with potatoes, as well in the enlighted cultures as the cultures performed in the dark.

The cultures grown on the medium with flour of oat provide mycelial thalli which are short-shaved, compact, heterogenous, and slightly coloured. Conidiogenesis did not practically occur.

MORPHOLOGICAL DATA OF FUSARIUM EQUISETI

Fusarium equiseti no. 213,107 shows the following particulars:
- lack of microconidias
- presence of macroconidias showing from 3 to 7 septa weared on branched macroconidiophors
- presence of intermediate chlamydospori, isolate or in chain.

The whole morphological data of the macroconidias, the lack of terminal chlamydospori and the presence of intermediate chlamydospori allow the identification of this Fusarium as a Fusarium of the subgenus Gibbosum. Among the three species included in this genus, only the species equiseti corresponds to this whole of morphological data. The appearance of the peach colour of the cultures and the oblong shape of the basal cells in form of foot, confirm this identification.

(B) Preparation of the first tank of the fermentation (1) culture on inclinated gelose The content of an ampul of lyophilizated mycelium is taken up with 2 ml sterile water. The thus obtained suspension is utilized for seeding 4 test tubes containing 10 ml of a solid medium containing:

| | |
|---|---|
| floaked oats | 30g |
| glucose | 10g |
| agar-agar | 20g |
| distilled water enough for | 1000ml |

This solution is sterilized by heating for 20 mn at 120° C. The pH of this medium is about 6,6 before sterilization and 5,8 after sterilization. These slides are incubated for 6 to 8 days in a thermostatic oven at 28° C. then let to receive the sunlight for a week at laboratory temperature.

(2) culture in a Roux's Flask

The aerial mycelium from a test tube is taken up with 10 ml sterile water. This suspension is utilized for seeding 5 Roux's Flasks containing 200 ml of the same medium containing gelose as in the first step. The incubation is carried out for 6 to 8 days in a thermostatic oven at 28° C. then subjected to enlightening in the sun light for a week at the laboratory's temperature.

(C) Preparation of the inoculates for the second tank (a) first stage

From the culture in a Roux's flask, a suspension of mycelium in 100 ml water is prepared by scraping the whole surface of the culture. This suspension is used for seeding a 10-liters Flask containing 4 liters of the following medium:

| | |
|---|---|
| saccharose | 25g |
| glucose | 25g |
| ammonium nitrate | 10g |
| mono potassic phosphate | 5g |
| magnesium sulphate | 2,5g |
| water enough for | 1000ml |

This solution is made sterile by heating it for 30 mn at 120°. The pH values decrease from 5,45 before sterilization to 4.75 after sterilization. The aerobic incubation is performed at 28° C. in a thermostatic jacket under bubbling of sterile air which insures the stirring for at least 48 h and better 72 hours.

(b) second stage

The seeding of the second tank is performed starting from the culture in the 10 liters flask to a tank containing 75 liters of the following medium:

| | |
|---|---|
| saccharose | 40g |
| celerose | 5g |
| ammonium nitrate | 10g |
| monopotassium phosphate | 5g |
| magnesium sulphate | 2,5g |
| water enough for | 1000ml | sterilization of this medium at 120° for 30 mn; pH after sterilization, 5.6.

The fermentation of this second stage is performed under a stream of sterile air of 3.5 m$^3$/h a stirring of 70 RPM, a temperature of 29° C.+1 for at least 36 hours.

During the fermentation, the controls of sterility, the determination of pH a nicroscopic evaluations and determination of the amounts of reducing sugars are performed on samples sterilely taken up.

(c) third stage

A sample of the cultures of the second stage is used for seeding 12,00l of the same milieu as previously (amount of culture: 6.25%).

| | |
|---|---|
| aeration | 70 m$^3$ per hour |
| stirring | 30 RPM |
| temperature | 29° C. + 1 |
| duration from | 36 to 40 h. |

The broth is submitted during this period to the same determination as previously exposed.

(D) Industrial Manufacture

The 12,00l of inoculum (3rd stage) are utilized as a whole to seed an industrial tank containing 7 m$^3$ of a medium having the following composition:

| | |
|---|---|
| saccharose | 50g |
| Celerose | 5g |
| ammonium nitrate | 10g |
| monopotassium phosphate | 5g |
| magnesium sulfate | 2.5g |
| zinc sulfate | .04g |
| calcium carbonate | .2g |
| tap water enough | 1 l |

This medium is sterilized by heating at 120° for 30 mn.

The pH of the medium after sterilization is about 6.5. This culture is carried under the following experimental conditions.

| | |
|---|---|
| aeration | 250 m³/h |
| stirring | 20 RPM |
| temperature | 29° C. + 1 |
| duration about | 40 hours |

The pH value is of about 3 at the 24th hour and increases steadily to reach the values of about 5.3, 5.5 at the end of the fermentation. After termination of the fermentation, the mycelium is separated from the broth by filtration. The mycelium is dried in a ventilated oven 120 Kg mycelium are obtained after drying and grinding.

(E) Extraction of the depsipeptide (1) Extraction of the raw product 100 kg of the ground dried mycelium previously obtained are taken up in 400 l trichlorethylene. After 2 hours stirring the unsoluble material is separated by filtration and pressed. This mass is a new washed with 100 l trichlorethylene then extracted a second time with 300 l trichlorethylene under stirring for one hour and filtered. The insoluble matters are further washed with 100 l trichlorethylene. The organic solutions are united, concentrated under reduced pressure until a thick mass is obtained. This mass is separated and weighs about 10 Kg.

It is further taken up in 90 liters hexane. The solution is filtered and the clear filtrate is extracted using a counter current device with aqueous methanol (methanol 80: water 20 vv). Once with 50 l, once with 25 l, for the third time with 12.5 l and for the fourth time with 10 l of the mixture. The methanolic solutions are united and distilled off until dry under reduced pressure.

(2) Purification of the raw product

1 Kg of alumina is suspended in 5 l water and concentrated hydrochloric acid is slowly added until the pH value reaches 4. The stirring is kept for 24 h while maintaining the pH at this value. Alumina is filtered on a gauze of nylon, washed with water then with acetone until dry and finally dried in an oven at 200° for a night.

20 Kg of the methanolic dry residue are dissolved in 80 liters methylene chloride and the solution is filtered. The filtrate is poored on a chromatography column filled with 40 Kg of alumina prepared as previously indicated and further washed with methylene chloride. The methylenic solution is slowly added at a speed of about 15 liters per hour. After completion of the addition the column is washed at the same rate with 80 liters of methylene chloride.

The methylenic eluates are recovered and concentrated until thick consistence. This paste is taken up in 200 liters ethanol, filtered until clear, cooled to 4° C. and slowly added to 400 liters distilled water. The addition of water lasts about 8 hours and the thus formed suspension is kept under stirring for 20 hours at 4° C. The precipitated crystals are separated by filtration, washed with 20 l of a mixture of ethanol: 1-water: 2 previously cooled at 4° then with 50 l water. The crystals are further dried at 40° C. in an oven under reduced pressure until constant weight.

The depsipeptide appears as a white crystalline powder, odourless and of bitter taste. It is sparingly soluble in water but easily soluble in chloroform, methanol and 95% ethanol.

The melting point of the anhydrous product determined on Koffler bank is about 121° (+5); Its rotatory power is $[\alpha]_D^{20} = -80°$ (+5) (C=5% methanol)

Nitrogen content: 6,2+0.3%

The infra-red spectrum in KBr is supplied with hereafter.

(3) Separation and identification of the four components by TLC

A solution of 10 mg/ml of the depsipeptide in methanol is prepared and 10 μl of this solution is deposited on a plate of 20 cm×20 cm charged with a mixture of cellulose Mn 300 and cellulose Mn 300 Q and impregnated with a mixture of formamide-acetone (1:4) until 2 cm from the top.

After development the plates are dried at 100° C. for 1 hour, and sprayed with a 0.5% chloroformic solution of iodine. The plates show 4 different yellow strains. The two most important have a Rf respectively of 0.55 and 0.45, one less important has a Rf of about 0.35 and the slighest one has a Rf of about 0.3.

(4) Separation of the components by HPLC

The percentages of the four components after HPLC have been determined with an integrator by reference to the square of the 4 peaks and assuming that the absorption in UV light at 254 mμ is the same for each component.

The HPLC in reverse phase has been carried out with a 30 cm long column filled with Bonsapak CL 8 ml in a Waters apparatus. The solvent of elution is a mixture of methanol 8V-water αv. The output of the eluents is of about 1.5 ml/mn and 10 μl of a 10 mg/ml solution of the depsipeptide in methanol is injected. The peaks are detected by measure of the absorbance at 254 mμ, and the squares thereof is measured with an integrator ICAP 5.

The results obtained correspond to the average of the values obtained with several samples of different productions of the depsipeptide.

| | |
|---|---|
| Compound A in average | 3.9 |
| Compound B in average | 15.3 |
| Compound C in average | 38.1 |
| Compound D in average | 42.7% |

The following graph shows the separation of the four components by HPLC

EXAMPLE II

Pharmaceutical compositions containing as active ingredient the depsipeptide from Fusarium equiseti.

(a) pressurized solution in Isopropyl Myristate

| | |
|---|---|
| Depsipeptide | .050g |
| Oil of Neroli | .050g |
| Eucalyptol | .050g |
| Saccharine | .00125g |
| Isopropyl Myristate enough for | 2.5ml |
| Flugene 12 as propellent | 7.5ml |

(b) aqueous suspension

| | |
|---|---|
| Depsipeptide | .050g |
| polyoxyethylenesorbitane mono oleate sold under the trade name "Tween 80" | .010g |
| Sodium chloride | .180g |
| Oil of Neroli | .050g |
| Eucalyptol | .050g |
| Sodium saccharinate | .010g |
| Water enough for | 20ml |

The two pharmaceutical compositions are packed in a flask fitted with a pump which delivers each time 0.080 g of solution or suspension i.e. 200 μg of active ingredient by delivered dosis.

(c) pressurized solution in Isopropyl Myristate

| | |
|---|---|
| Depsipeptide | .015g |
| Flavouring agent | .0075g |
| Isopropyl Myristate enough for | .75ml |
| Freon 12 | 2.25ml |

This solution is packed in a container fitted with a valvedelivering 25 μl each time. The amount of depsipeptide delivered at each pulverization is of about 125 μg.

(d) pressurized solution in Isopropyl Myristate

| | |
|---|---|
| Depsipeptide | .030g |
| Flavouring agent | .015g |
| Isopropyl Myristate | .75ml |
| Freon 12 | 2.25ml |

This solution is packed in a container fitted with a valve delivering 250 μg of depsipeptide each pulverization. This container is intended for 120 pulverizations.

(e) Solution in oil

| | |
|---|---|
| Depsipeptide | .05g |
| Saccharine | .0015g |
| Flavouring agent | .05g |
| Isopropyl Myristate enough for | 6ml |
| Propelling agent | .05g 2ml |

The container is fitted with a valve delivering 30 μl each time.

(f) aqueous suspension

| | |
|---|---|
| Depsipeptide | .050g |
| polyoxyethylenesorbitane mono oleate (sold under the trade name "Tween 80") | 120mg |
| Potassium chloride | 3mg |
| Disodium phosphate | 17.25mg |
| Dipotassium phosphate | 3mg |
| Calcium chloride | 1.5mg |
| Magnesium chloride | 1.5mg |
| Sodium Mercurithiolate | .0375mg |
| Water enough for | 15ml |
| Propellent enough | |

-continued

This suspension is packed in a container fitted with a pump delivering 75 μl at each pulverization.

Each pulverization then provides 250 μg of active ingredient.

(g) injectible aqueous suspension

| | |
|---|---|
| Depsipeptide | 100mg |
| Cremophor EL | 100mg |
| Sodium chloride | 800mg |
| Sterile water enough for | 100ml |

This suspension is packed in ampuls of 1 ml each containing 1 mg active ingredient per unit dosage.

EXAMPLE III

Pharmacological study of the depsipeptide of this invention

(A) Study of the stimulation of the humoral immunity in the mice after sensibilization with red blood cells of the sheep This test is performed on batches of 10 mice of swiss CD strain weighing about 20 g. Each mouse receives a threshold immunizing dosis of 10 millions of red blood cells by intravenous way.

The mice are treated at various periods of time before immunization either by intravenous or intraperitoneous way. The depsipeptide from Fusarium equiseti is dissolved in propylene glycol (84 mg/ml) then this concentrated solution is diluted with a saline solution. The mice are injected with 10 or 50 μg of depsipeptide.

A lot of controls receives only the red blood cells and the solvent.

A lot of mice receives a suspension of a culture of Corynebacterium simplex in a saline solution as a reference product.

The bloods of the mice are taken at the established days through retroorbital ponction. The sera are stored at −80° C. For each batch the sera are tested individually as well as a pool of sera.

DETERMINATION OF THE CONTENT IN ANTIBODIES (a) determination of the hemagglutinine titer 0.05 ml of a suspension of red blood cells of sheep in the Mayer buffer, titrating 7.107 cells/ml is added to 0.025 ml of serum diluted in a saline s solution. The plates are placed for two hours at room temperature in a closed vessel then for a night at +4°. The hemagglutinations are evidenced by reading through a magnifier lens. The hemagglutinizing titer is calculated from the highest dilution of the serum providing a clear hemagglutination. It is expressed using the exponent at the log 2 of this dilution (for example dilution 1/64 titer=6)

The clear hemagglutinations are only shown from titer=4, the lowest values being usually not clearly concluding.

(b) determination of the hemolytic titer 0.025 ml of a suspension of red blood cells of sheep in the Mayer's buffer ($10^8$/ml) are added to 0.025 ml of guinea pig's complement previously diluted in the Mayer's buffer (1/200) and to 0.025 ml serum diluted with saline solution ($\frac{1}{2}, \frac{1}{4}, \frac{1}{8} \ldots$)

The plates are placed in an oven at 37° for 1 hour then at +4° C. for 2 hours. The determination is effected by means of a glass.

The hemolytic titer is appreciated as the highest dilution of the serum causing the complete lysis of the red blood cells of sheep. It is expressed in the same fashion as the hemagglutining titer.

RESULTS

(1) Study on the threshold dosis

Several dosis of red blood cells of sheep have been tested in order to determine the minimal dosis which causes an humoral answer in the swiss mice and provokes a supraliminal answer. The maximal answer obtained with $10^8$ red blood cells/mouse is magnified by the immunostimulant agents. Moreover $10^6$ red blood cells do not provoke any sensible humoral answer. In contrast thereof $10^7$ red blood cells/mouse give a homoral answer the cinetic of which is of value for the testing of the immunostimulant agents.

The threshold dosis may vary broadly without any scientific explanation.

(2) Study of the kinetics in the controls and in reference animals

Several batches of controls which receive only $10^7$ red blood cells/mouse have been studied from a point of view of kinetics and have shown that the hemagglutinizing antibodies appear from the fourth day after immunization for certain batches and from the seventh day for other batches. The hemagglutining titers are usual lower than 4. It appears also that the hemolytic titers of the sera of the controls are practically equal to zero until the seventh day.

Cultures of corynebacterium parvum have been used as a reference substance and show they stimulate the immunological answer being injected 3 to 6 days before the injection of red blood cells. Antibodies appear in immunostimulated animals on the fourth day. 14 days after the significance of the immunological answer is statistically of greater value.

(3) Study of the depsipeptide from Fusarium equiseti

The depsipeptide from Fusarium equiseti has been administered to mice during 3 days from the 6th to the third day before injection of red blood cells. It provokes an increase in the content of hemolytic and hemagglutining antibodies together with an induction in the appearance of hemolytic antibodies from the fourth day after injection of red blood cells.

Doses from 10 μg to 50 μg/day/mouse cause the same result. The immunostimulation caused by the depsipeptide is of the same order of that caused with 500 μg/day of cultures of corynebacterium parvum (Institute Pasteur of Paris). The same results have been obtained with the depsipeptide with doses which are 10 to 50 times lower than those of corynebacterium parvum.

(B) Lymphoblastic transformation Test (TTL)

The determination of the lymphoblasts by administration of the depsipeptide from Fusarium equiseti has been carried out using the method described by R. P. Danicle and S. K. Hollan Proceed Nat. Acad Sci (New York) 73, (1976) 3599. This test is performed at the optimal concentration of the mitogenic agent, the product to be tested remaining in contact with the cells during the whole set of time. Under this experimental conditions the, incorporation of the biological precursor is quite reproductible and maximal. The biological effect produced by the product is evidenced by inhibition of the incorporation of the tagged inhibitor.

The determination of the optimal doses of the mitogenic agent is based on the curves Effect/Doses using the beginning of the plateau.

The reference substances are Phytohemagglutinin (optimal dosis 1 μg/ml) and lipopolysaccharides of Escherichia coli (optimal dosis 5 μg/ml)

From the results hereafter exposed, it appears that in contrast to the reference substances the depsipeptide from Fusarium equiseti is not a mitogenic agent at the tested doses and curbes the incorporation of tritiated Thymidine usually induced by the mitogenic agents.

(C) Study of the effects of the depsipeptide from Fusarium equiseti on the immunological response Depending on the administered doses the tested substance show a stimulant or depressant effect either on the humoral or cellular immunological answer in the mice.

The humoral answer has been evidenced after administration of lipopolysaccharide from Escherichia coli (Vujanovic 1973-Le Bouteiller 1974) which increase the amount of blood cells of medullar aspect.

The cellular response has been evidenced after administration of ethoxymethylene oxazolone according to the methods described by Turk (1967) and Anderson (1972).

The characteristics of the cells from an immunological and ultrastructural point of view have been determined according to the method of Jeannesson (1975)

The number of white blood cells producing the antibodies is quantitatively determined using the test of hemolysis zones in a semi solid medium containing the target red blood cells. This test utilizes the zones of direct hemolysis according to the method of Jerne and Nordin (1963) which detect the cells producing Ig M In view of the auto-radiographie study, the suspensions of cells are incubated at 37° C. with tritiated thymidine at a dosis of 20 μCi/ml for 30 minutes before being treated for the determination of the Ig M of surface.

The cells are fixed with glutaraldehyde then stained with diaminobenzidine according to the method of Graham and Karnovsky (1966), then treated with osmic acid and inbedded into EPON.

RESULTS

Immunological response to ethoxymethylene oxazolone (a) number of cells

On the 5th day after administration of the depsipeptide from Fusarium equi seti the increase of the number of cells is usually higher than 50 percent, namely after intraperitoneal administration in the mice. On the 9th day the increase is slightly less significant and thereafter discontinues. The number of cells having incorporated some tritiated thymidine is of the same order by controls and tested animals, i.e. of about 4–6%.

(b) number of cells able to recognize the antigenic substances

On the 5th day the percentage of cells recognizing the antigenic substance is very significantly increased (257 percent) and this increase results both from an increase of the amounts of cells in the ganglions and an increase of the percentage of the cells specifically activated for a determined number of cells ($10^6$ cells). This increase progressively disappears and cannot be evidenced after the 9th day.

(c) number of cells forming zones of hemolysis

The very significant increase of cells forming zones of hemolysis appears on the 5th day and is caused by an increase in the number of the cells. On the 9th day this increase namely results from the number of cells forming hemolysis zones for a determined number of cells ($10^6$ cells).

(d) effect on the content in antibodies

On the 5th day the content in antibodies remain constant from the beginning. On the 9th day the percentages of hemagglutining antibodies and of hemolyzing antibodies is broadly increased namely that of hemolyzing antibodies.

(e) study on the number of cells having Ig on their surfaces

The cells having Immunoglobulines (Ig) at their surface have been counted on their slides from the initial cellular suspension in the controls and in the treated mice. The percentage is of about 35 percent.

From a microscopic inspection it appears that the nature of the cells causing hemolysis and the cells forming rosettes are the same in the controls and in the treated mice. For the rosette forming cells they are lymphokystes with Ig on their surface and white T cells the proportion of which reaches 40 to 50 percent on the 9th day. For the hemolysis zones forming cells they are namely plasmocyts.

IMMUNOLOGICAL RESPONSE AFTER PRETREATMENT WITH LIPOPOLYSACCHARIDES

The injection of the depsipeptide from Fusarium equiseti induces a slight increase in the number of cells on the 9th day.

The effect on cells recognizing the antigenic substance is none and even negative. The decrease of the cells able to recognize the antigenic substance is more significative on and after the 9th day.

No effect has been evidenced on the number of cells forming hemolysis zones.

A slight decrease in the content of hemagglutining antibodies appears whilst an important increase in the content of hemolyzing antibodies is shown on the 5 th day.

CONCLUSION

The immunological effects of the depsipeptide from Fusarium equiseti may be summarized in the following fashion.

Immunological response to ethoxymethylene oxazolone is increased. The increase of the cells in or around the ganglions is significant and maximal on the 5th day (50 to 80%). The number of cells recognizing the antigenic substance is very frequently increased either due to the increase of the number of cells or due to the increase in this specific activity. The increase in the hemolysis zones forming cells reflects only the increase in the number of cells in the ganglions.

The immunological response after pretreatment with lipopolysaccharides is decreased. The number of cells recognizing the immunogenic agent remains constant or is decreased. The content in antibodies is decreased or remain unaltered.

(D) Effect of the depsipeptide on the immunological response.

(1) Potentializing action on the humoral immunity.

This test has been performed on batches of 10 mice (C 57 B6 male mice strain) which are injected each with 300 μg of purified bovine serum albumine (fraction V of Cohn), purchased from the Armour Pharmaceutical Company, in the posterior plantar paws.

At the first day 20 mice received each 0.2 ml of a mixture containing the solution of BSA in a phosphate buffer and 10 μg of the depsipeptide from Fusarium equiseti (2 vol) and Freund's uncomplete adjuvant (3 vol).

A batch of 10 mice is used as controls. It receives only the same mixture but the depsipeptide and the Freund's adjuvant.

Anoter batch receives only the injection of BSA together with the Freund's adjuvant.

At the day 21 the half of the mice in each bath is sacrifized to determine the content of anti BSA-antibodies by passive hemagglutination. The second half of the mice receives a reniewed injection of the mixture at half dosage (0.1 ml instead of 0.2 ml).

At the day 35 the remaining mice are sacrifized and the content of specific anti BSA antibodies is determined using the same method.

A very significant increase in the content of specific antibodies is evidenced on the 35th day in the treated mice.

(2) Effects on the cellular immunological response.

(a) mitogenic potency of the depsipeptide 500.000 splenic lymphokytes from CBA strain mice suspended in 0.1 ml RPMI are incubated at 37° C. for 3 days in a stream of carbonic anhydride with various concentrations of the depsipeptide from Fusarium equiseti.

In the same fashion the white cells are also incubated with phytohemagglutinine at a concentration of 1/200, Concanavaline at a concentration of 10 μg/ml as reference substances.

4 hours before the termination of this incubation period, 1 μCi tritiated thymidine is added to each culture. Afer completion of the incubation the cells are filtered and twice washed with saline solution. The radio activity on the filter is counted with a β-ray counter. The incorporation of Thymidine is calcuated as the ratio between the amount of incorporated thymidine in the presence of the mitogenic substance and the amount of incorporated thymidine in the lymphokytes without any mitogenic substance.

RESULTS

The following results have been obtained and are tabulated hereinafter:

The results show that the depsipeptide curbs the nucleic metabolism at very low dosages through a very strong effect on the immunosuppressive cells or a modification of the metabolism or cellular permeability.

The depsipeptide is not a mitogenic substance as such. In contrast thereof, it may have a stimulant effect on the lymphokytes in the presence of the usual mitogenic substances.

| Amount of active substance | Ratio of incorporation | Statystical value |
|---|---|---|
| 0,1 pg/ml = | 0,41 (± 0,1) | p = 0,0047 |
| 1 pg/ml = | 0,62 (± 0,07) | p = 0,044 |
| 5 pg/ml = | 0,84 (± 0,06) | Not significative |
| 10 pg/ml = | 0,90 (± 0,06) | Not significative |
| 110 pg/ml = | 0,32 (± 0,12) | p = 0,0078 |
| 1 ng/ml = | 0,40 (± 0,10) | p = 0,0082 |
| 10 ng/ml = | 0,56 (± 0,08) | Not significative |
| 100 ng/ml = | 0,62 (± 0,07) | Not significative p = 0,054 |
| 1 µg/ml = | 0,36 (± 0,1) | p = 0,0044 |
| 10 µg/ml = | 0,63 (± 0,07) | p = 0,028 |
| 100 µg/ml = | 0,80 (± 0,06) | Not significative |
| PHA 1/200 = | 51,15 (± 0,006) | p = 0,0028 |
| ConA 10 µg = | 50,30 (± 0,006) | p = 0,0025 |
| LPS 100 µg = | 14,81 (± 0,012) | p = 0,0028 |

(b) stimulation of the activities of the macrophages

The peritoneal macrophages from unstimulated rats (Fisher strain) are prelevated through peritoneal washing and isolation on plastic rack. They are cultivated for a night with dosages of the depsipeptide ranging from 1 picogramm to 1 nanogramm/ml.

The content in proteins, in lysosomal $\beta$-glucoronidase, and in cytoplasmic leucine-amino peptidase are determined on the cells previously lysed with 0.05% Triton X-100.

In the same manner, incubation has also been performed with a solution of lipopolysaccharide from Escherichia coli and Muramyldipeptide as reference substances.

The depsipeptide induces a significant increase of the hydrolases in the macrophages at a dose ranging from 1 pg to 10 ng/ml. The proteic content is also increased with doses ranging from 10 to 100 pg/ml. As higher doses and namely from 100 ng/ml the depsipeptide appears to be toxic for the cells as evidenced by the strong decrease in the proteic content and the increase in the content of intracellular macrophagic enzymatic activities.

The same test has also been performed in vitro. The rats received 6 days before the peritoneal washings an intrapeitoneal injection of depsipeptide (1 to 100 µg in 1 ml saline solution).

Lipopolysaccharides from Escherichia coli Muramyl dipeptide and water soluble adjuvant are injected to other batches of rats as reference substances. The peritoneal macrophages recovered after washings are incubated for 2 hours in order to delete the non-adhering cells and further for 4 hours. The cells are then lysed and the enzymatic and proteic contents determined as above given.

RESULTS

At a dosis of 1 µg the depsipeptide from Fusarium equiseti induces a very high increase of the lysomal enzymes ($\beta$-glucuronidase+35%) and of the cytoplasmic enzymes (leucine amino peptidase+35%). The content in proteins is also increased (+24%). At this dosis the water soluble adjuvant induces an increase of the hydrolases of 39% and the lipopolysaccharides an increase of 42% of the leucine aminopeptidase and 35% of the proteins. These activities are thus of about the same level.

In contrast thereof at a dosis of 100 µg the depsipeptide induces an increase of 32% of the protein content and of 50% of the cytoplasmic enzymes. These activities are far higher than those of the other immunostimulating agents.

At a dosis of 1 ng the stimulation is weaker.
protein content, +11%
$\beta$-glucouronidase, +23%
leucine amino peptidase, +16%

The following tables summarized the various results obtained with several doses of the depsipeptide in comparison with the reference substances.

TABLE I

| | | 1 µg | P | 100 µg | P |
|---|---|---|---|---|---|
| Depsipeptide | Proteins | + 24% | = 0,0125 | + 32% | 0,005 |
| | $\beta$-Glucuronidase | + 35% | 0,025 | + 37% | 0,025 |
| | L.A.P. (leucine amino-peptidase) | + 35,5% | 0,025 | + 59% | 0,0025 |
| L.P.S. | Proteins | + 35% | 0,01 | + 14% | 0,025 |
| | $\beta$-Glucuronidase | − 14% | 0,025 | − 3% | N.S. |
| | L.A.P. | + 42% | 0,001 | + 2% | N.S. |
| M.D.P. | Proteins | + 7,5% | N.S. | + 2% | N.S. |
| | $\beta$-Glucuronidase | + 27% | 0,01 | + 5% | N.S. |
| | L.A.P. | + 24% | 0,025 | + 5% | N.S. |
| W.S.A. (Water soluble adjuvant) | Proteins | + 3,6% | N.S. | + 1% | N.S. |
| | $\beta$-Glucuronidase | + 39% | 0,001 | + 46% | = 0,001 |
| | L.A.P. | − 10,5% | = 0,025 | − 7% | N.S. |

Amounts of cellular enzymes and proteins in the macrophages after 16 hours incubation.

TABLE II

| | | Depsipeptide | Lipopoly-saccharide | Muramyl-dipeptide |
|---|---|---|---|---|
| Saline | Proteins | 45.7 ± 0,1 | 46.0 ± 1,1 | 46,0 ± 1,1 |
| | $\beta$-glucuronidase | 29,5 ± 0,1 | 29,1 ± 2,2 | 29,1 ± 2,2 |
| 1 pg/ml | Proteins | 44,9 ± 4,2 NS | 55,1 ± 2,2[b] | 46,1 ± 2,2 NS |
| | $\beta$-glucuronidase | 35,8 ± 1,9[c] | 39,2 ± 1,5[b] | 36,5 ± 0,1[b] |
| 10 pg/ml | Proteins | 53,3 ± 4,3[b] | 47,7 ± 2,2 NS | 44,8 ± 0,7 NS |
| | $\beta$-glucuronidase | 35,4 ± 4,8[c] | 37,1 ± 5,8[a] | 36,3 ± 6,4 NS |
| 100 pg/ml | Proteins | 50,1 ± 4,2[b] | 52,2 ± 6,3 NS | 44,6 ± 1,9 NS |
| | $\beta$-glucuronidase | 33,0 ± 2,4[c] | 38,7 ± 9,9 NS | 41,0 ± 2,9[b] |

TABLE II-continued

|  |  | Depsipeptide | Lipopoly-saccharide | Muramyl-dipeptide |
|---|---|---|---|---|
| 1 ng | Proteins | 48,2 ± 4,3 NS | 45,0 ± 0,4 NS | 44,0 ± 1,8 NS |
|  | β-glucuronidase | 34,2 ± 3,7[c] | 21,0 ± 0,5[a] | 34,0 ± 5,3 NS |
| 10 ng/ml | Proteins | 45,9 ± 1,4 NS | 47,1 ± 0,4 NS | 43,4 ± 1,8 NS |
|  | β-glucuronidase | 32,8 ± 5,6[b] | 25,2 ± 6,6 NS | 39,6 ± 6,1[a] |
| 100 ng/ml | Proteins | 44,3 ± 4,0 NS | 52,3 ± 0,4[b] | 40,5 ± 0,7[b] |
|  | β-glucuronidase | 29,8 ± 8,8 NS | 34,9 ± 3,4[a] | 23,9 ± 6,2 NS |
| 1 ng/ml | Proteins | 44,2 ± 5,9 NS | 46,5 ± 1,3 NS | 45,1 ± 0,9 NS |
|  | β-glucuronidase | 27,1 ± 0,3[c] | 26,0 ± 2,1 NS | 30,6 ± 3,8 NS |
| 10 ng/ml | Proteins | 41,9 ± 7,0[b] | 43,7 ± 2,5 NS | 48,1 ± 1,8 NS |
|  | β-glucuronidase | 25,2 ± 9,3[b] | 23,4 ± 1,7[c] | 32,2 ± 3,0 NS |
| 100 ng/ml | Proteins | 36,6 ± 5,6[c] | 41,2 ± 3,8[b] | 55,3 ± 3,1[b] |
|  | β-glucuronidase | 7,5 ± 3,5[c] | 11,6 ± 2,4[c] | 39,0 ± 1,6[c] |

The content in proteins is expressed in g/$10^6$ cells and that in β-glucuronidase in mMol of substrate hydrolysed by $10^6$ cells per hour.

Degrees of statistical significance

| a | = | p 0,05 |
| b | = | p 0,025 |
| c | = | p 0,001 |
| NS | = | without signification |

(3) Effect on the release of chromium induced in the larvae of schistosoma mansoni after treatment by an immunostimulant agent.

The depsipeptide from Fusarium equiseti has been tested to determine its action in vivo on the cytotoxicity induced in the intraperitoneal macrophages of the rat against the larvae of schistosoma mansoni.

The macrophages are stimulated either in vitro or in vivo and are contacted with a suspension of larvae of schistosoma mansoni previously tagged with 51 chromium.

Cytotoxicity in vivo

This contact is intended to demonstrate an optional cytotoxic effect measured by the amounts of chromium released in the culture medium. This measure reflects the significance of cellular lesions on the surface of the schistosomules. The radio activity released in the medium is expressed as a percentage of the total radioactivity present in the schistosomules at the beginning of the experiments.

The obtained results are summarized in the table III

| Substances | 1 ng | 1 g | 100 g |
|---|---|---|---|
| Depsipeptide | +0,5% (NS) | +13% (NS) | +10% (NS) |
| Lipopolysaccharides |  | +24% (p 0.025) | +50% (p 0.005) |
| Muramyldipeptide |  | +6% (NS) | +10% (NS) |
| WSA |  | +23% (p 0.025) | +30% (p 0.025) |

The despsipeptide causes a release of 51 Cr but it is not statistically significant; it is also for Muramyldipeptide the same.

The lipopolysaccharides and the WSA make the macrophages significantly more toxic for the larvae as are the macrophages of untreated animals.

The depsipeptide is practically devoid of any effect on the macrophages in vivo against the schistosomules.

CYTOTOXICITY IN VITRO

After incubation for 24 hours of normal macrophages it is not any increase of the cytotoxicity of the macrophages against the tagged schistosomules. The doses of depsipeptide which stimulate the macrophages induce only a slight decrease of the release of the tagged tracer.

The table IV explained the obtained results

| | Release of 51 Cr | | | |
|---|---|---|---|---|
| Saline | 100 pg/ml | 1 ng/ml | 10 ng/ml | 100 ng/ml |
| 24.03% (± 2.4) | 19.67% ± 3.1 | 18.21% ± 3.9 | 21.71% ± 3.5 | 23.46 ± 2.7 |

(4) Action of the depsipeptide on the survival time of the mice after injection of leukemic cells L 1210

Due to the fact that the depsipeptide from Fusarium equiseti acts as an immunostimulant in vivo and acts namely as activating the macrophages (as does BCG), it appears of value to study comparatively these two substances.

As a model they are utilized batches of mice inoculated with leukemic cells L 1210 and previously treated with Cyclophosphamide. The injection of the depsipeptide or of BCG allows the determination of their action on the residual action disease.

METHOD

This test has been performed in batches of mice (strain BDF) of 7–8 weeks old. The animals are treated according to the method described by Mathé and Cowork "Immunotherapie active des cancers" (ESP Paris 1976)

At the day 0 all the animals receive intravenously a suspension of 1000 leukemic living cells L 1210.

At the day 1 the animals are divided in 4 lots of 10 animals of the same weight. The controls receive only the saline solution by intraperitoneal way. The three other batches receive intraperitoneously an injection of cyclophosphamide at the suboptimal dose of 80 mg/Kg. The batches which receive the cyclophosphamide are further treated in the following manner:

one batche receives intravenously 0.1 ml of saline solution at the day +6. This batch is merely intended to determine the time of survival of the mice previously treated by the cyclophosphamide.

one batch receives intravenously an injection of 1 mg/mouse of BCG (Institut Pasteur) in 0.1 ml saline solution.

They are intended to show the effects of the active immunotherapy after administration of cyclophosphamide, BCG appearing as an active agent in these experimental conditions.

another batch receives intraperitoneously 50 μg Depsispeptide/mouse in 0.5 ml saline solution. They are intended to determine the survival time of the mice treated by the depsipeptide from Fusarium equiseti.

For each batch the survey of the mice is maintained for 40 days. The role of each product on the survival time is estimated and the statistical significance is determined using the test "t" of student by comparing the results of each batch to those of the controls and if necessary with the results obtained with the treated batches.

RESULTS

The results obtained in this test are gathered in table V. Cyclophosphamide at suboptimal dosis extends in a statiscally significative manner, the survival time of the animals. The mixture cyclophosphamide-BCG merely improves the survival time in a non statistically significative manner.

The mixture cyclophosphamide-depsipeptide provokes a statistically significative improvement of the survival time in the thus treated animals. However no significative difference can be seen between the results from the two batches treated with the mixture of therapeutic agents (cyclophosphamide+BCG and cyclophosphamide+depsipeptide)

This test shows that the depsipeptide from Fusarium equiseti increases the survival time of the mice previously injected with 1000 L1210 living leukemic cells and treated with cyclophosphamide. The results are of the same order than those obtained with BCG the number of animals used in this experiment is to small to establish a statistically significative differentiation.

Moreover it has been determined in the mice that a single injection of the depsipeptide from Fusarium equiseti (50 to 250 μg) induces the appearance of Hassal's corpuscules in the thymus and the appearance of the germinative center in the spleen.

DETERMINATION OF THE ACUTE TOXICITY

The average lethal dosis of the depsipeptide has been determined on batches of 10 heteroxenic mice (strain CD) or on batches of 10 rats (strain Wistar). All the animals receive the depsipeptide either in aqueous suspension or in a solution into Isopropyl Myristate.

This compound is administered orally, intraperitoneously or intravenously at increasing dosages. The animals are kept under survey for 8 days, and the deathes when they are any, are numbered. The average lethal dosis is graphically determined using the method of Lichtfield and Wilcoxon.

The thus obtained results are hereinafter summarized:

(a) aqueous suspension

| | |
|---|---|
| in the mice orally | $LD_{50}$ = 5000 mg/Kg |
| intraperitoneously | $LD_{50}$ = 67 mg/Kg |
| intravenously | $LD_{50}$ = 17 mg/Kg |
| in the rats orally | $LD_{50}$ = 5000 mg/Kg |
| Intraperitoneously | $LD_{50}$ = 67 mg/Kg |
| intravenously | $LD_{50}$ = 11 mg/Kg |

(b) solutions in Isopropyl Myristate

-continued

| | |
|---|---|
| in the mice intraperitoneously | |
| male mice | $LD_{50}$ = 169 mg/kg |
| female mice | $LD_{50}$ = 182 mg/Kg |
| in the mice intravenously | |
| male mice | $LD_{50}$ = 41 mg/Kg |
| female mice | $LD_{50}$ = 41 mg/Kg |

The phenomena of toxicity after intraperitoneal or intravenous injection are namely due to the physical state of the suspended particules in the aqueous medium.

When dissolved in isopropyl Myristate the toxicity of the depsipeptide is largely decreased.

What we claim is:

1. A mixture of peptidolic substances obtained from the mycelium of Fusarium equiseti, said mixture being separable into four components by high pressure liquid chromatography, said components being designated A, B, C & D, said mixture, on acidic hydrolysis yielding α-hydroxy iso valeric acid and N-methyl Valine; N-methyl isoleucine and N-methyl allo iso leucine, and on alkaline hydrolysis yielding the lactone of α hydroxy isovaleroyl N-methyl Valine, the lactone of α-hydroxy isovaleroyl N-methyl isoleucine and the lactone of α-hydroxy iso valeroyl N-methyl allo iso leucine.

2. A mixture according to claim 1 in which the proportion by weight of the four components designated A, B, C & D ranges from 2 to 5% for component A, from 10 to 16% for component B, from 32 to 38% for component C and from 40 to 47% for compound D.

3. The component D of the biological substance according to claim 1.

4. The component of claim 3 which upon complete acid hydrolysis yields three moles of a member selected from the group consisting of N-methyl isoleucine and N-methyl allo isoleucine per mole of component B and, upon alcaline hydrolysis yields, per mole of component D, three moles of a lactone selected from the group consisting of lactone of alpha hydroxy isovaleroyl N-methyl isoleucine or alpha hydroxy isovaleroyl N-methyl allo iso leucine.

5. A process for producing a compound of claim 1 which comprises the steps of aerobically fermenting a culture of Fusarium equiseti, separating the mycellium from the broth, drying said mycelium and extracting said dried mycelium with a water insoluble organic solvent, separating the organic phase, and removing the solvent therefrom, to form a residue taking up the residue in a liquid hydrocarbon and exhaustively extracting said hydrocarbon solution with aqueous alkanol, separating the aqueous alkanol, removing the solvent therefrom to yield a residue, drying said residue, purifying said residue by chromatography on alumina, concentrating the chromatographic eluate, dissolving said concentrated eluate in an alkanol, adding water to said alkanolic solution and removing the precipitated crystalline compound of claim 1 therefrom.

6. A process according to claim 5 in which the Fusarium equiseti is a mutant species designated as Fusarium Equiseti (Corda) saccardo filed at The Commonwealth Mycological Institute at Kew (GB) under the filing number 213,107.

7. A biological substance from the mycelium of Fusarium equiseti 213,107 whenever obtained in or by process of claim 5.

8. A process of claim 5 comprising the additional purification step of separating the products into four components by high pressure liquid chromatography.

9. The pharmaceutical compositions containing as active ingredient the biological substance of claim 1 in admixture or conjunction with an inert non toxic pharmaceutically-acceptable carrier or vehicle.

10. The pharmaceutical compositions of claim 9 wherein the inert carriers or vehicles are those suitable for administration by the parenteral the percutaneous, the permucous and the rectal routes.

11. A pharmaceutical composition according to claim 11 wherein the amount of active ingredient ranges from 0.05 to 1 mg per unit dosage.

12. A pharmaceutical composition containning as active ingredient the biological substance of claim 10 in admixture or conjunction with an inert non toxic pharmaceutically-acceptable carrier or vehicle.

13. A method for treating or curbing the immunological reactions in the men or animals suffering from disturbances in the defences of the organism, which consists in administering to said patients a safe but effective amount of the biological substance from the Mycelium of a Fusarium according to claim 1.

14. A method of stimulating humoral immune defenses in subjects suffering from a deficiency of such defenses by administering to said subjects an effective amount of a substance of claim 1.

15. The method of claim 14 wherein the safe but effective amount of the active ingredient ranges from 0.2 to 5 mg per day in the man.

16. A method of reducing immune reactions in a subject exhibiting a hypersensitivity to same by administering to said subject an effective amount of the substance of claim 1.

17. The method of claim 16 wherein the safe but effective amount of the active ingredient ranges from 0.2 to 5 mg per day in the man.

* * * * *